United States Patent
Heaton et al.

(10) Patent No.: US 7,279,612 B1
(45) Date of Patent: Oct. 9, 2007

(54) WOUND TREATMENT APPARATUS EMPLOYING REDUCED PRESSURE

(75) Inventors: Keith Patrick Heaton, Poole (GB); Kenneth William Hunt, Merley (GB)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 10/009,294

(22) PCT Filed: Apr. 20, 2000

(86) PCT No.: PCT/GB00/01566

§ 371 (c)(1),
(2), (4) Date: Jun. 6, 2002

(87) PCT Pub. No.: WO00/64394

PCT Pub. Date: Nov. 2, 2000

(30) Foreign Application Priority Data

Apr. 22, 1999 (GB) ................... 9909301.5

(51) Int. Cl.
*A61F 13/00* (2006.01)
(52) U.S. Cl. ............... 602/42; 602/3; 602/46; 604/289; 604/304
(58) Field of Classification Search ............ 602/3, 602/41–43, 46, 48; 604/289–291, 292, 304–308, 604/313–316, 48; 128/888, 889
See application file for complete search history.

(56) References Cited

U.S. PATENT DOCUMENTS

| | | |
|---|---|---|
| 3,066,672 A | 12/1962 | Crosby, Jr. et al. |
| 3,520,300 A | 7/1970 | Flower |
| 4,098,268 A * | 7/1978 | Scott ............... 602/3 |
| 4,178,924 A * | 12/1979 | Baxter ............... 602/3 |
| 4,335,488 A | 6/1982 | Becker |
| 4,548,202 A | 10/1985 | Duncan |
| 4,710,165 A | 12/1987 | McNeil et al. |
| 4,758,220 A | 7/1988 | Sundblom et al. |
| 4,768,501 A * | 9/1988 | George ............... 602/6 |
| 4,826,494 A | 5/1989 | Richmond et al. |
| 4,969,880 A | 11/1990 | Zamierowski |
| 5,086,170 A | 2/1992 | Luheshi et al. |
| 5,092,858 A | 3/1992 | Benson et al. |
| 5,134,994 A | 8/1992 | Say |
| 5,215,522 A | 6/1993 | Page et al. |
| 5,278,100 A | 1/1994 | Doan et al. |

(Continued)

FOREIGN PATENT DOCUMENTS

AU 745271 3/2002

(Continued)

OTHER PUBLICATIONS

PCT International Search Report; PCT international application PCT/GB98/02713; Jun. 8, 1999.

(Continued)

*Primary Examiner*—Kim M. Lewis

(57) ABSTRACT

Apparatus is described for stimulating healing of wounds, particularly burns, to the hands or feet. The apparatus comprises an envelope for receiving the affected part of the body. The envelope (12) comprises an air-tight cover which contains a porous pad (22, 24, 26) for covering the wound. Means are provided for connecting the interior of the envelope to a source of suction.

20 Claims, 4 Drawing Sheets

U.S. PATENT DOCUMENTS

| | | | |
|---|---|---|---|
| 5,279,550 | A | 1/1994 | Habib et al. |
| 5,342,376 | A | 8/1994 | Ruff |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,636,643 | A | 6/1997 | Argenta et al. |
| 5,865,772 | A * | 2/1999 | George ............................ 602/3 |
| 6,051,747 | A * | 4/2000 | Lindqvist et al. ............. 602/46 |
| 6,241,747 | B1 | 6/2001 | Ruff |
| 6,345,623 | B1 | 2/2002 | Heaton et al. |
| 6,398,767 | B1 * | 6/2002 | Fleischmann ............... 604/313 |
| 6,553,998 | B2 | 4/2003 | Heaton et al. |
| 6,814,079 | B2 | 11/2004 | Heaton et al. |
| 2002/0077661 | A1 | 6/2002 | Agarwel, et al. |

FOREIGN PATENT DOCUMENTS

| | | |
|---|---|---|
| AU | 755496 | 12/2002 |
| CA | 2005436 | 6/1990 |
| DE | 1093 949 | 12/1960 |
| DE | 26 40 413 A1 | 3/1978 |
| DE | 43 06 478 A1 | 9/1994 |
| DE | 295 04 378 U1 | 9/1995 |
| EP | 0 046 560 A1 | 3/1982 |
| EP | 0117632 A2 | 1/1984 |
| EP | 0161865 | 11/1985 |
| EP | 0358 302 | 3/1990 |
| EP | 1 018 967 B1 | 8/2004 |
| GB | 692578 | 6/1953 |
| GB | 2 197 789 A | 6/1988 |
| GB | 2 220 357 A | 1/1990 |
| GB | 2 235 877 A | 3/1991 |
| GB | 2 307 180 A | 5/1997 |
| GB | 2333965 A | 8/1999 |
| GB | 2329127 B | 8/2000 |
| GB | 2 351 025 A | 12/2000 |
| RU | 2 029 563 C1 | 2/1995 |
| RU | 2 126 692 C1 | 2/1999 |
| RU | 2 240 763 C2 | 11/2004 |
| RU | 2082367 C1 | 4/2007 |
| SG | 71559 | 4/2002 |
| WO | WO80/02182 | 10/1980 |
| WO | WO93/09727 | 5/1993 |
| WO | WO/94/20041 | 9/1994 |
| WO | WO96/05873 | 2/1996 |
| WO | WO97/18007 | 5/1997 |
| WO | WO99/13793 | 9/1998 |

OTHER PUBLICATIONS

PCT Written Opinion; PCT international application PCT/GB98/02713; Jun. 8, 1999.

PCT International Examination and Search Report, PCT international application PCT/GB96/02802; Jan. 15, 1998 and Apr. 29, 1997.

PCT Written Opinion, PCT international application PCT/GB/96/02802; Sep. 3, 1997.

Kostyuchenok, B.M, et al. ;Vacuum Treatment in the Surgical Management of Purulent Wounds; Vestnik Khirurgi, Sep. 1986.

Davydov, Yu. A., et al; Vacuum Therapy in the Treatment of Purulent Lactation Mastitis; Vestnik Khirurgi, Sep. 1986.

Yusupov, Yu. N., et al; Active Wound Drainage, Vestnik Khirurgi, vol. 138, Issue 4, 1987.

Davydov, Yu. A., et al; Bacteriological and Cytological Assessment of Vacuum Therapy of Purulent Wounds; Vestnik Khirurgi, Oct. 1988.

Davydov, Yu. A., et al; Cocepts For the Clinical-Biological Management of the Wound Process in the Treatment of Purulent Wounds by Means of Vacuum Therapy; Vestnik Khirurgi.

International Search Report for PCT international application PCT/GB95/01983; Nov. 23, 1995.

Patent Abstract of Japan; JP4129536; Terumo Corporation; Apr. 30, 1992.

Orringer, Jay, et al., "Management of Wounds in Patients with Complex Enterocutaneous Fistulas", Surgery, Gynecology & Obstertics, Jul. 1987, V. 165, pp. 79-80.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp.: 1-5.

* cited by examiner

WOUND TREATMENT APPARATUS EMPLOYING REDUCED PRESSURE

BACKGROUND OF THE INVENTION

1. Field of the Invention

The present invention relates to an apparatus for the healing of wounds and more particularly to preventing progression of partial-thickness burns.

2. Description of Related Art

Where a person suffers a burn, the dermal and epidermal layers in the region of the wound are damaged. Closure of the resulting wound is important to prevent loss of body fluids and invasion by micro-organisms. In the case of a partial-thickness burn, epithelial and subcutaneous tissue adjacent to the wound will migrate outwards and eventually grow new tissue over the wound. A wide array of wound coverings has been developed to expedite wound closure and allow the natural processes of repairing the damaged tissue to proceed.

The prognosis of a wound caused by a burn depends on the severity of the injury and particularly the depth of the burn. In general, a partial-thickness burn will heal more quickly and with less complications than a deeply penetrating burn. It has been observed that partial-thickness burns often deteriorate and become more serious, deeper burns, if not treated promptly after incurring the burn injury.

The hands more often suffer burn injuries than other parts of the body. Probably, this is due to the natural reaction of attempting to protect the face with the hands and, in many cases, the burn injury is to the back of the hands. Other parts of the body which more frequently suffer burns may be the arms, feet and legs.

The present invention seeks to provide apparatus for treating injuries to a part of the body, especially injuries caused by burns.

BRIEF SUMMARY OF THE INVENTION

According to one aspect of the invention there is provided an apparatus for stimulating healing of wounds which comprises an envelope for receiving an affected part of the body, said envelope including a substantially air-tight cover and a porous pad within the cover, said cover being adapted to contact the wound surface, and connection means for connecting the interior of the envelope to a source of negative pressure.

By substantially "air-tight" cover is meant one which is sufficiently air-tight that by applying suction to the porous pad, a pressure below ambient can be maintained within the envelope. It is not, however, necessary for the material of the envelope to be totally air occlusive.

It has been found that when negative pressure therapy using the apparatus of the invention is applied to a burn within a relatively short time of incurring the injury (e.g. within about 12 hours), not only is the rate of healing improved but progression of a partial-thickness burn to a deeper injury is arrested.

In one embodiment, the apparatus of the invention, the envelope comprises a glove, sleeve or sock. For example, the apparatus may include a glove formed from a flexible plastics or rubber foam which is contained within a cover of low air-porosity. Typically, the flexible plastics foam is a polyurethane or polyvinyl alcohol (pva) foam having intercommunicating cells or a combination of such foams, e.g. as a laminate. In such a laminate, the pva layer may be adjacent the wound.

BRIEF DESCRIPTION OF THE SEVERAL VIEWS OF THE DRAWINGS

Additional features of the present application will become apparent from the following description and accompanying drawings, in which.

DETAILED DESCRIPTION OF THE INVENTION

The embodiment shown in the accompanying drawings is designed for use in treating burns to the hand.

It will be appreciated that various appropriate modifications are possible for treating burns to other parts of the body, such as feet, are within the scope of the invention.

Figure 1:
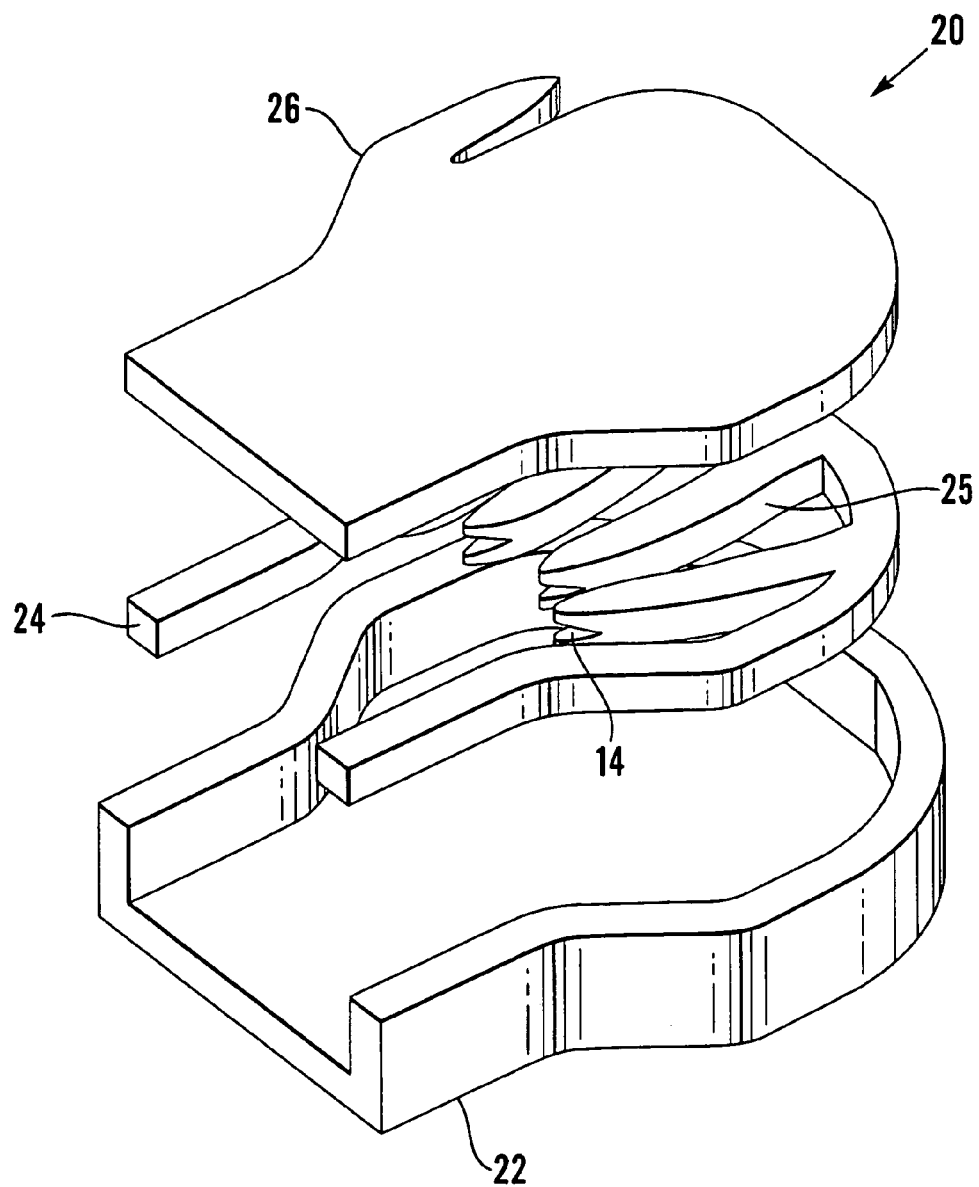
FIG. 1 is an exploded perspective view of the porous pad.
Figure 2:
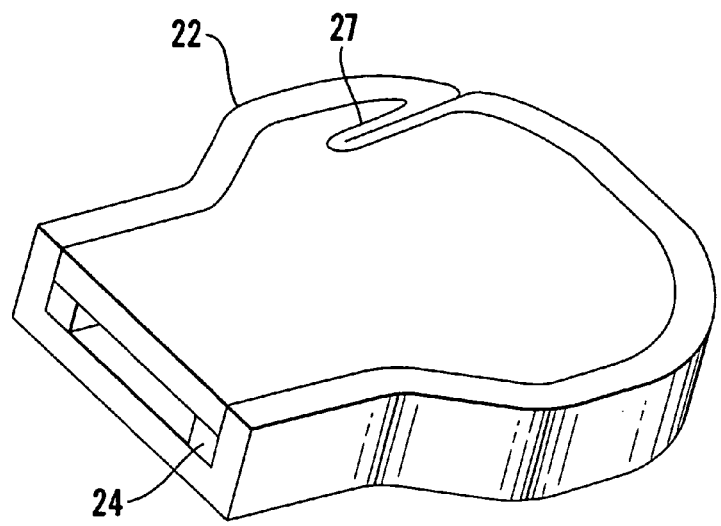
FIG. 2 is a perspective view when the porous pad is assembled together.
Figure 3:
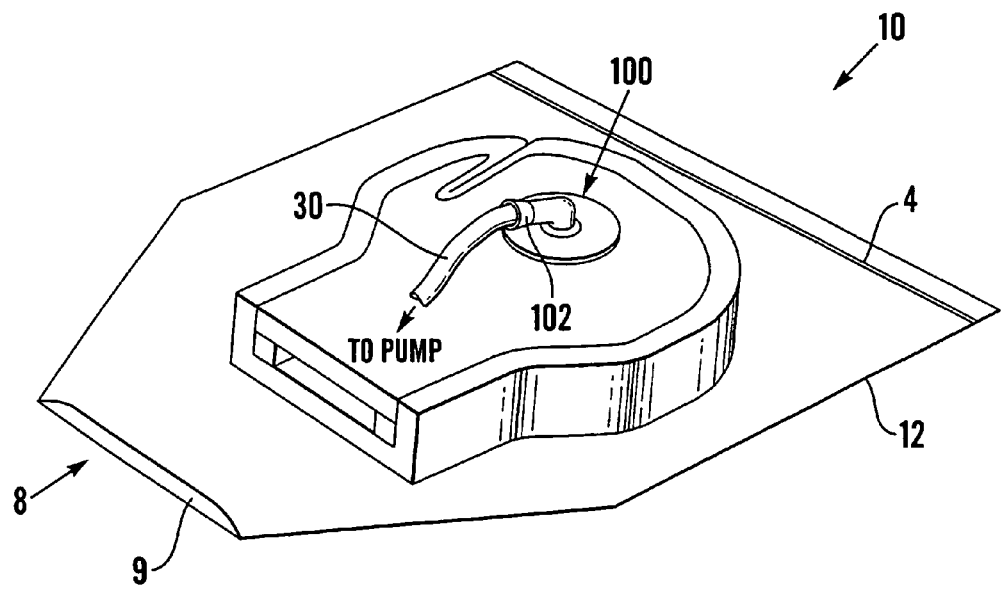
FIG. 3 is a perspective view of the porous pad within its cover.
Figure 4A:
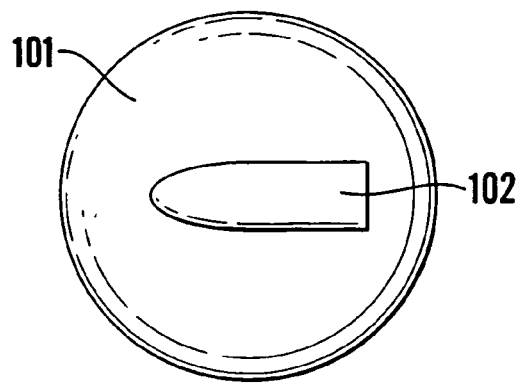
FIGS. 4a to 4d show various views of a connector for pneumatically connecting the porous pad to a source of negative pressure.
Figure 4B:
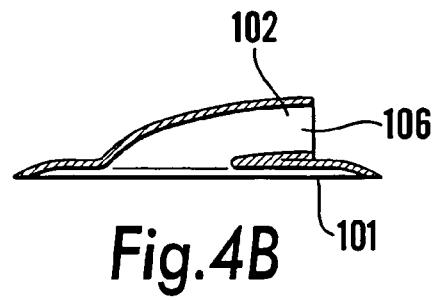
Figure 4C:
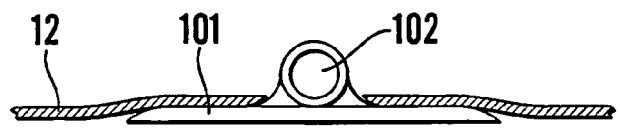
Figure 4D:
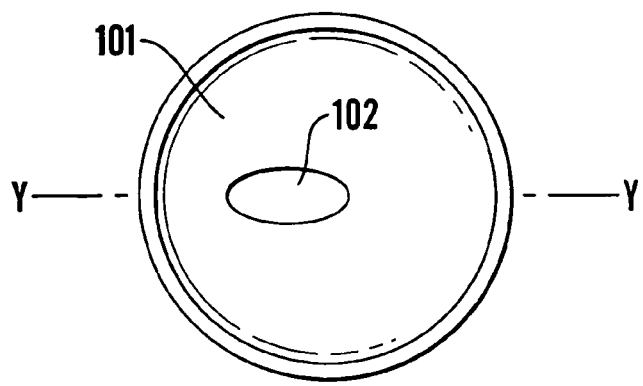

FIGS. 1, 2 and 3 show apparatus (10) for treating wounds to the hands comprising a porous pad having a lower base (22), a middle section (24) and an upper section (26) incorporated within a cover (12) of low air porosity. The porous pad is in the form of a glove or mitten and may be constructed by fixing the upper section (26) to the base (22) while retaining the middle section (24) within the cavity so formed. Typically, the porous pad is a reticulated plastics foam, and may be formed by gluing or welding the separate sections together. When placed inside the pad, the hand is held in place with fingers spread by finger-separators (25) and V-cut type grooves (14). As shown in FIGS. 2 and 3, the foam may be shaped to provide for a separate supporting compartment (27) for the thumb to aid the attainment of the optimum positions of the fingers and thumb for healing. However, this is not essential. The pad is preferably made from a reticulated foam such as polyurethane as described in PCT application WO 96/05873, polyvinylalcohol foam or a combination thereof.

FIG. 3 shows the assembled pad after insertion into a cover (12). Cover (12) is an envelope formed from airimpermeable sheet material, e.g. polyurethane or polyolefin film, and is sized to encompass the glove-shaped porous pad. The distal end of the cover (12) has a large opening (not shown) which is closable by an easily re-sealable means (4) such as a zip-type seal used on food bags. The proximal end (8) includes a substantially impermeable pressure-sensitive acrylic resin adhesive (9), the underside of which is secured as an air-tight seal to the patient's skin. The proximal end (8) may be coated on its inner surface with a pressure-sensitive acrylic resin adhesive (9) in order to seal the cover to the patient's skin, e.g. at the wrist or lower arm. Alternatively, the proximal end (8) may be sealed to the patient's wrist with a separate piece of adhesive tape, such as a polyurethane film coated with a pressure-sensitive adhesive. The proximal end (8) is open and is tapered as shown. By providing a taper, the proximal end can be cut to a size such that the opening will fit snugly around the patient's wrist. Attached to the cover (12) in the region of a central part of the porous pad is a connector (100). Connector (100) may be attached to the cover by adhesive.

Figure 5:
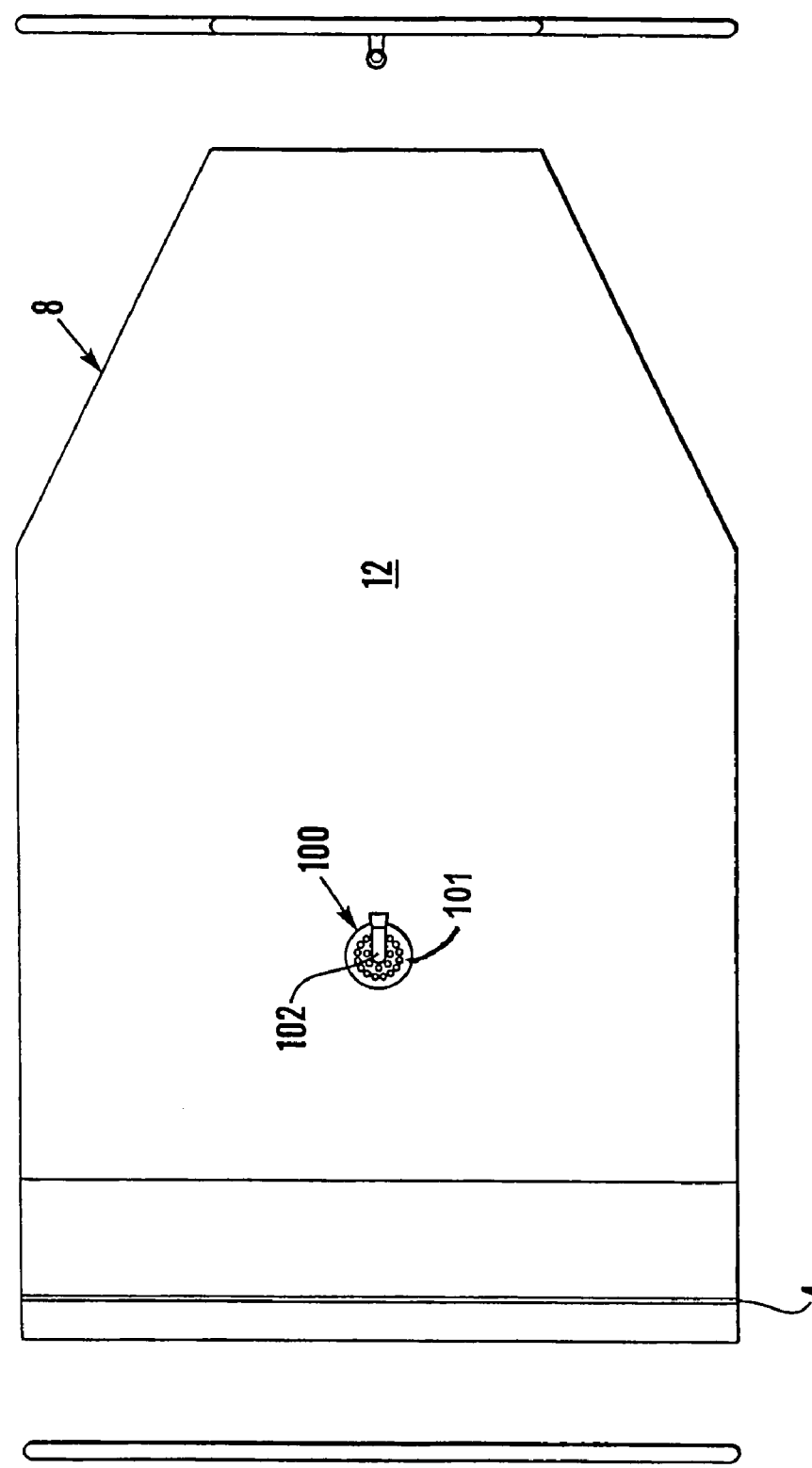
FIG. 5 is a plan view of a modified cover.

FIG. 5 is a plan view of a cover similar to cover (12) shown in FIG. 3. The same reference numerals are used to indicate corresponding parts. The cover shown in FIG. 5 differs from that shown in FIG. 3 in that the end (8) for attachment at the patient's wrist has a somewhat larger taper and is designed so that the end can be trimmed to suit the patient. The connector (100) has a generally circular flange (101) whose underside face (i.e. the face which in use contacts the foam page 20) is formed with small projecting buttons. The construction of this aspect of the connector is as described in GB Patent Application No. 2,333,965. Instead of using a zip lock seal, a seal of the "Velcro" type can be used. In this embodiment, a zip lock seal (4) is formed from polyethylene and this is joined to the rest of the cover, which is formed from polyurethane, by adhesive tape.

FIGS. 4a to 4d show various views of the connector (100) and it will be seen that it comprises a molded plastics flange portion (101) and suction port having a centrally positioned spout (102) and aperture (106). The connector (100) is firmly attached to the cover by an adhesive. The spout extends through a hole cut in the cover and the upper surface of the flange (101) is bonded with adhesive to the cover (12). The spout (102) is sized to accept as a closely sliding fit, the end of a single or multi-lumen tube (30) (FIG. 3) which emerges from beneath the wound cover (12). Tube (30) may be constructed as described in co-pending patent application WO 97/18007. Where a multi-lumen tube is used, one lumen can be used for measuring the pressure at the burn site. It is also within the scope of this invention to irrigate the burn or other wound through one of the lumens or via a separate connector to the foam pad. The connector or connectors can be used to introduce drugs, e.g. antibiotics, to the wound site. The cover drape (12) is preferably made from a flexible film of low air permeability such as polyurethane and may include a protective layer of polyethylene. Suitable materials are described in GB Patent Application No. 2,333,965.

In use, the hand of a patient having a burn injury is introduced into the outer cover (12) via the end (8). Re-sealable opening (4) may then be opened and folded back to expose the injured hand. The hand is then introduced into the porous pad which may be pre-assembled or assembled in situ around the injured hand. In the latter case, it may be convenient to fix the upper section (26) to the lower section base (24) by suturing or stapling, rather than gluing or welding the foam. With the foam pad in place encompassing the injured hand, the cover (12) is drawn over the porous pad and the opening (4) re-sealed. Spout (102) is then connected by a tube to a suction pump, e.g. using the technique described in WO 97/108007. Pulsed, intermittent or continuous negative pressure may be applied to the patient's hand in accordance with a program which may be controlled automatically by a control device associated with the pump as described in our above patent application. Negative pressure therapy using the apparatus of the invention has been found to stimulate healing of burns and to reduce the progression of cell death beneath a burn injury. Also, by improving blood flow to the wound area, infection is controlled and granulation of the wound is stimulated.

One additional beneficial effect of therapy using the apparatus of this invention is that during therapy, the hand is held firmly in a half-closed position, which is the optimum position for promotion of healing. This can be further encouraged by the introduction of a rigid or semi-rigid splint, e.g. of plastics, which is formed or molded into the desired shape, the collapsed dressing being strapped to the splint during or after application of the suction, so that the desired healing position can be maintained after release of the suction.

The suction pump is perfectly controlled by control means including a pressure transducer for monitoring pressure at the wound site as described in our above PCT application. A timer device may also be associated with the pump to provide on/off operation if necessary at selected intervals. The apparatus may also include a canister located between the porous pad and the pump to collect wound exudate. Typically, the pump is a diaphragm pump but other types of pumps and equivalent components, such as vacuum bottles may be substituted. The apparatus may also be used with a wall suction source as described in GB Patent Application No. 2,342,584.

The terms and expressions which have been employed are used as terms of description and not of limitation. Although the present invention relates mainly to partial-thickness burns, it is understood that the present invention maybe used with open wounds as well as a possible treatment of pressure sores.

The invention claimed is:

1. Apparatus for stimulating healing of wounds which comprises an envelope for receiving an affected part of the body, said envelope including a substantially air-tight cover and porous pad within the cover, said pad being adapted to contact the wound surface, and connection means for connecting the interior of the envelope to a source of negative pressure, wherein the cover has a re-sealable opening which permits the wound to be inspected at intervals.

2. Apparatus as claimed in claim 1, wherein the source of negative pressure is a suction pump.

3. Apparatus as claimed in claim 1, wherein the source of negative pressure is positioned outside the envelope and fluidly connected to the connection means.

4. Apparatus as claimed in claim 1, wherein the substantially air-tight cover is air impermeable.

5. Apparatus as claimed in claim 1, wherein the porous pad comprises a foam having intercommunicating cells.

6. Apparatus as claimed in claim 1, wherein the envelope comprises a flexible plastic.

7. Apparatus as claimed in claim 1, wherein the porous pad comprises polyurethane foam.

8. Apparatus as claimed in claim 1, wherein the connection means comprises a flange bonded to the cover, a spout, and an aperture.

9. Apparatus for stimulating healing of wounds which comprises an envelope for receiving an affected part of the body, said envelope including a substantially air-tight cover and porous pad within the cover, said pad being adapted to contact the wound surface, and connection means for connecting the interior of the envelope to a source of negative pressure, which includes a canister for collecting wound exudate.

10. Apparatus as claimed in claim 9, wherein the source of negative pressure is a suction pump.

11. Apparatus as claimed in claim 9, wherein the source of negative pressure is positioned outside the envelope and fluidly connected to the connection means.

12. Apparatus as claimed in claim 9, wherein the substantially air-tight cover is air impermeable.

13. Apparatus as claimed in claim 9, wherein the porous pad comprises a foam having intercommunicating cells.

14. Apparatus as claimed in claim 9, wherein the envelope comprises a flexible plastic.

15. Apparatus as claimed in claim 9, wherein the porous pad comprises polyurethane foam.

16. Apparatus as claimed in claim 9, wherein the connection means comprises a flange bonded to the cover, a spout, and an aperture.

17. An apparatus for stimulating healing of wounds, comprising:

an envelope for receiving an affected part of the body, said envelope including a substantially air-tight cover and porous pad within the cover, the pad being adapted to contact the wound surface, and a connector fluidly connected to the interior of the envelope and to a source of negative pressure, wherein the cover has a re-sealable opening which permits the wound to be inspected at intervals.

18. Apparatus as claimed in claim 17, wherein the source of negative pressure is positioned outside the envelope.

19. An apparatus for stimulating healing of wounds, comprising:

an envelope for receiving an affected part of the body, said envelope including a substantially air-tight cover and porous pad within the cover, the pad being adapted to contact the wound surface, and a connector fluidly connected to the interior of the envelope and to a source of negative pressure; and a canister for collecting wound exudate.

20. Apparatus as claimed in claim 19, wherein the source of negative pressure is positioned outside the envelope.

* * * * *